(12) United States Patent
Nakaso

(10) Patent No.: US 8,166,799 B2
(45) Date of Patent: May 1, 2012

(54) GAS CONCENTRATION DISTRIBUTION MEASURING APPARATUS

(75) Inventor: Noritaka Nakaso, Tokyo (JP)

(73) Assignee: Toppan Printing Co., Ltd, Tokyo (JP)

( * ) Notice: Subject to any disclaimer, the term of this patent is extended or adjusted under 35 U.S.C. 154(b) by 484 days.

(21) Appl. No.: 12/379,998

(22) Filed: Mar. 5, 2009

(65) Prior Publication Data

US 2009/0229344 A1 Sep. 17, 2009

(30) Foreign Application Priority Data

Mar. 7, 2008 (JP) ................................. 2008-058278

(51) Int. Cl.
*G01N 29/02* (2006.01)
(52) U.S. Cl. ...................................... 73/24.01; 73/23.23
(58) Field of Classification Search .................. None
See application file for complete search history.

(56) References Cited

U.S. PATENT DOCUMENTS

| | | | |
|---|---|---|---|
| 6,566,787 B2 * | 5/2003 | Tsukahara et al. ........ 310/313 R |
| 2004/0062684 A1 * | 4/2004 | McGee et al. ............... 422/68.1 |
| 2004/0189148 A1 * | 9/2004 | Yamanaka et al. ........ 310/313 R |
| 2004/0194533 A1 * | 10/2004 | Bohm et al. .................. 73/23.34 |
| 2006/0214537 A1 * | 9/2006 | Nakaso et al. ............ 310/313 R |

FOREIGN PATENT DOCUMENTS

JP 2007-271577 10/2007

* cited by examiner

*Primary Examiner* — Hezron E Williams
*Assistant Examiner* — Mark A Shabman

(57) ABSTRACT

A gas concentration distribution measuring apparatus includes a gas detection part, a gas detector position information measuring part, and a gas concentration distribution display unit. The detection part includes gas detectors provided at mutually different positions to measure a concentration of a predetermined gas, and moves while maintaining relative positions of the detectors. The position information measuring part measures position information of the detectors of the detection part. And, measured values of gas concentrations measured by the detectors of the detection part and position information of the detectors measured by the position information measuring part when the detectors finish measurement of gas concentrations are inputted in the display unit, then the display unit displays a distribution of concentrations of the predetermined gas in a space in which the detection part moves, based on the measured values of the gas concentrations and the position information of the detectors.

17 Claims, 7 Drawing Sheets

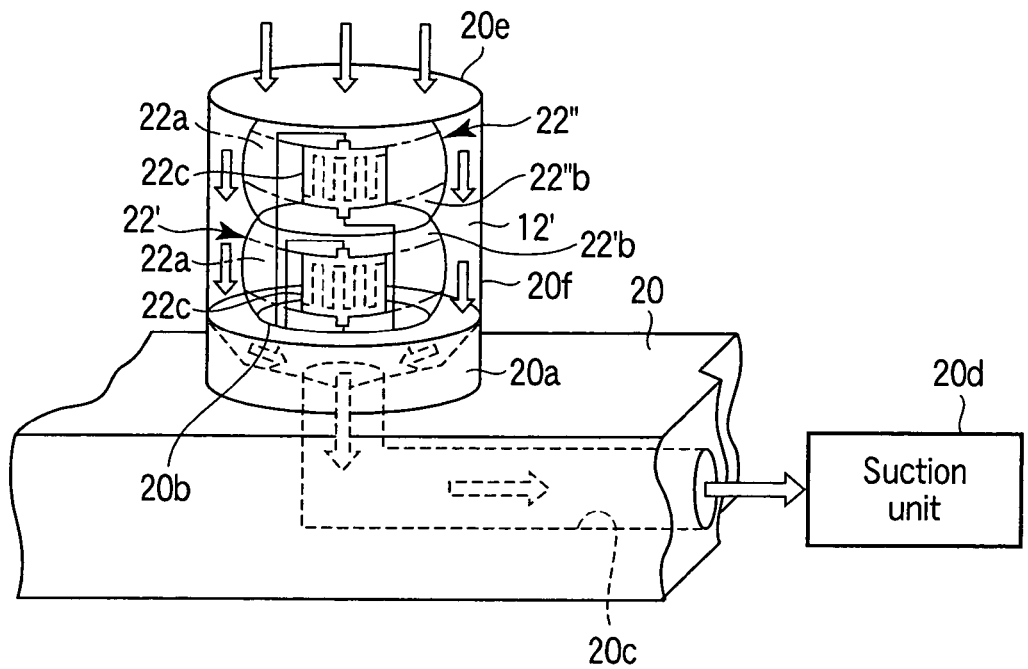
F I G. 5
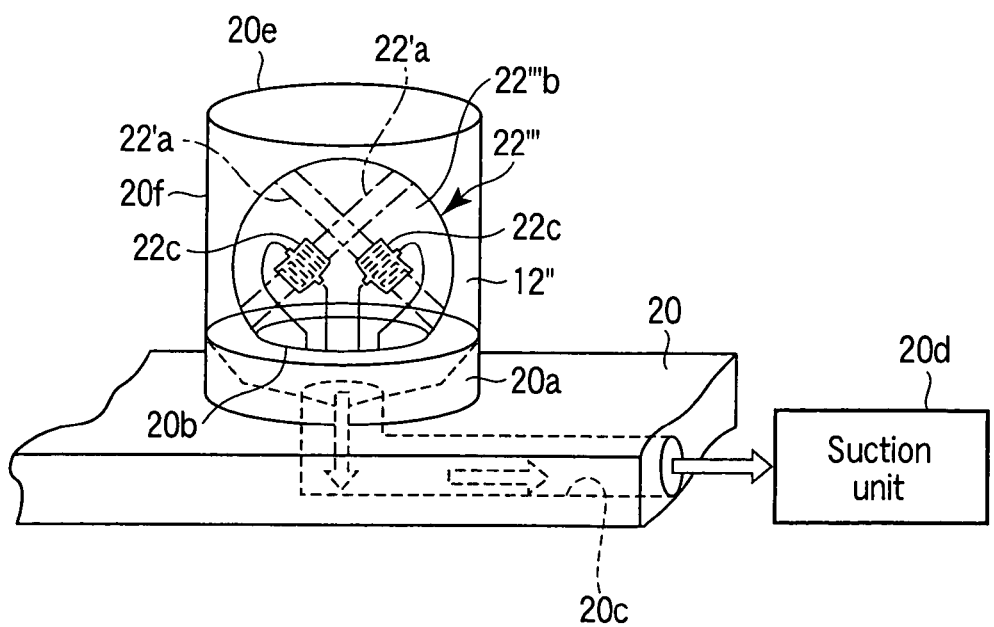
F I G. 6

GAS CONCENTRATION DISTRIBUTION MEASURING APPARATUS

CROSS-REFERENCE TO RELATED APPLICATIONS

This application is based upon and claims the benefit of priority from prior Japanese Patent Application No. 2008-058278, filed Mar. 7, 2008, the entire contents of which are incorporated herein by reference.

BACKGROUND OF THE INVENTION

1. Field of the Invention

The present invention relates to a gas concentration distribution measuring apparatus which measures a concentration distribution of a gas in a space.

2. Description of the Related Art

An inexpensive and portable gas concentration distribution measuring apparatus which is capable of measuring a concentration distribution of a gas in a space more precisely and faster has been demanded.

Currently, various gas concentration distribution measuring apparatuses, each of which uses a semiconductor type gas detector and has a size that can be held by a single hand and is capable of measuring concentration of a predetermined gas, are known. Among various conventional semiconductor type gas detectors, some take a relatively long time to measure the concentration of a predetermined gas and others can measure the concentration of a predetermined gas in a short time.

It will take a long time to measure the concentration distribution of a predetermined gas in a space by using only one gas concentration distribution measuring apparatus using only one semiconductor type gas detector that takes a relatively long time to measure the concentration of the predetermined gas, and it is highly probable that the concentration distribution of the predetermined gas in the space significantly changes while the concentration distribution of the predetermined gas is measured.

By using a plurality of gas concentration distribution measuring apparatuses each of which uses only one semiconductor type gas detector that takes a relatively long time to measure the concentration of a predetermined gas, the time needed to measure the concentration distribution of the predetermined gas in a space can significantly be reduced. However, it is still probable that the concentration of the predetermined gas in the space changes while they measure the concentration distribution of the predetermined gas. In addition, since the plurality of gas concentration distribution measuring apparatuses is used, preparations for measuring the concentration distribution of the predetermined gas become complicated.

Then, in order to measure the concentration distribution of a plurality of types of gases in a space, a plurality of gas concentration distribution measuring apparatuses each using only one semiconductor type gas detector to measure the concentration of a specific gas in order to measure the concentration distribution of a specific gas in the space are required and thus, still more gas concentration distribution measuring apparatuses are needed in proportion to the number of gases for which concentration measurement is needed.

Even if a gas concentration distribution measuring apparatus which uses a plurality of semiconductor type gas detectors to measure the concentrations of a plurality of types of gases is used, as described above, a plurality of gas concentration distribution measuring apparatuses need to be used to measure the concentration distributions of a plurality of types of gases in a space and thus, a preparation work for measuring the gas concentration distribution still complicated. In addition, if the semiconductor types gas detectors each of which takes a relatively long time to measure the concentration of a predetermined gas are used, it is probable that the concentration distributions of the plurality of types of gases in the space change during measurement.

A semiconductor type gas detector which is capable to measure the concentration of a predetermined gas in a short time utilizes the fact that the value of electric resistance of tin oxide changes with a change in concentration of a predetermined gas. However, such a semiconductor gas detector takes some time to respond to lowering of concentration of the predetermined gas. In addition, when such a semiconductor gas detector is used, it is necessary to heat tin oxide to a high temperature. Therefore, such a semiconductor type gas detector cannot be used for measuring the concentrations of a plurality of types of gases containing a combustible gas. Further, even if such a semiconductor gas detector is used for measuring the concentrations of a plurality of types of gases containing no combustible gas, tin oxide heated to a high temperature causes convection of a gas around the tin oxide and therefore limits a precision of measurement of the concentration distribution of the plurality of types of gases.

BRIEF SUMMARY OF THE INVENTION

According to an aspect of the present invention, a gas concentration distribution measuring apparatus comprises a gas detection part, a gas detector position information measuring part, and a gas concentration distribution display unit. The gas detection part includes a plurality of gas detectors provided at a plurality of mutually different positions to measure a concentration of a predetermined gas, and moves while maintaining relative positions of the plurality of gas detectors. The gas detector position information measuring part measures position information of the plurality of gas detectors of the gas detection part. And, measured values of gas concentrations measured by the plurality of gas detectors of the gas detection part and position information of the plurality of gas detectors measured by the gas detector position information measuring part when the plurality of gas detectors finish measurement of gas concentrations are inputted in the gas concentration distribution display unit, then the gas concentration distribution display unit displays a distribution of concentrations of the predetermined gas in a space in which the gas detection part moves, based on the measured values of the gas concentrations and the position information of the gas detectors.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is an enlarged perspective view schematically showing a first modification of one of the plurality of gas detectors in the gas detection part of the gas concentration distribution measuring apparatus in FIG. 1;

FIG. 6 is an enlarged perspective view schematically showing a second modification of one of the plurality of gas detectors in the gas detection part of the gas concentration distribution measuring apparatus in FIG. 1;

DETAILED DESCRIPTION OF THE INVENTION

First Embodiment

At first, a gas concentration distribution measuring apparatus 10 according to the first embodiment of the present invention will be described with reference to FIGS. 1 to 4.

Figure 1:
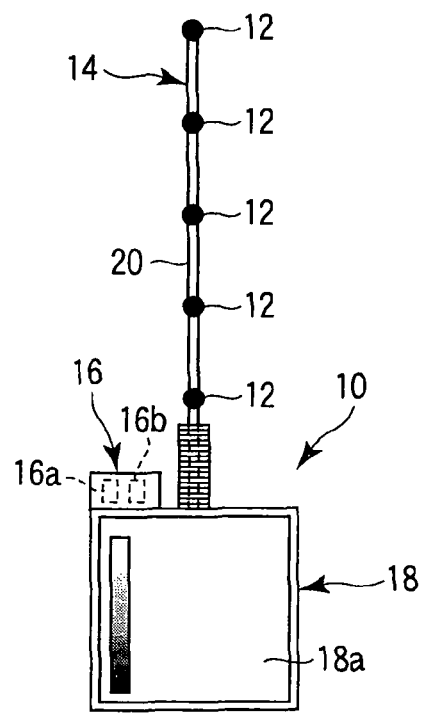
FIG. 1 is a schematic front view of the whole of a gas concentration distribution measuring apparatus according to a first embodiment of the present invention.

In FIG. 1, the front view of the whole of the gas concentration distribution measuring apparatus 10 according to the first embodiment of the present invention is shown.

The gas concentration distribution measuring apparatus 10 comprises: a gas detection part 14 which includes a plurality of gas detectors 12 provided at a plurality of mutually different positions to measure a concentration of a predetermined gas, and which moves while maintaining relative positions of the plurality of gas detectors 12; a gas detector position information measuring part 16 which measures position information of the plurality of gas detectors 12 of the gas detection part 14; and a gas concentration distribution display unit 18 to which measured values of gas concentrations measured by the plurality of gas detectors 12 of the gas detection part 14 and position information of the plurality of gas detectors 12 measured by the gas detector position information measuring part 16 when the plurality of gas detectors 12 finish measurement of gas concentrations are inputted, and which displays a distribution of concentrations of the predetermined gas in a space, in which the gas detection part 14 moves, based on the measured values of the gas concentrations and the position information of the gas detectors 12.

The plurality of gas detectors 12 in the present embodiment are supported on a linear rod shaped supporting member 20 at predetermined intervals (in this embodiment, predetermined equal intervals) and one end portion of the rod shaped supporting member 20 is fixed to a predetermined position of an outer housing of the gas concentration distribution display unit 18.

The gas detector position information measuring part 16 is also fixed to the outer housing of the gas concentration distribution display unit 18. The gas concentration distribution display unit 18 includes a display device 18a exposed on an outer surface of the outer housing, and in this embodiment the display device 18a is a liquid crystal display device.

The gas detector position information measuring part 16 includes at least one of a known acceleration sensor 16a and angular velocity sensor 16b, and, in this embodiment, both the known acceleration sensor 16a and angular velocity sensor 16b is included. Each of the acceleration sensor 16a and the angular velocity sensor 16b is operable at least in two directions along the X axis and the Y axis and, further preferably in one more direction along the Z axis.

Figure 2:
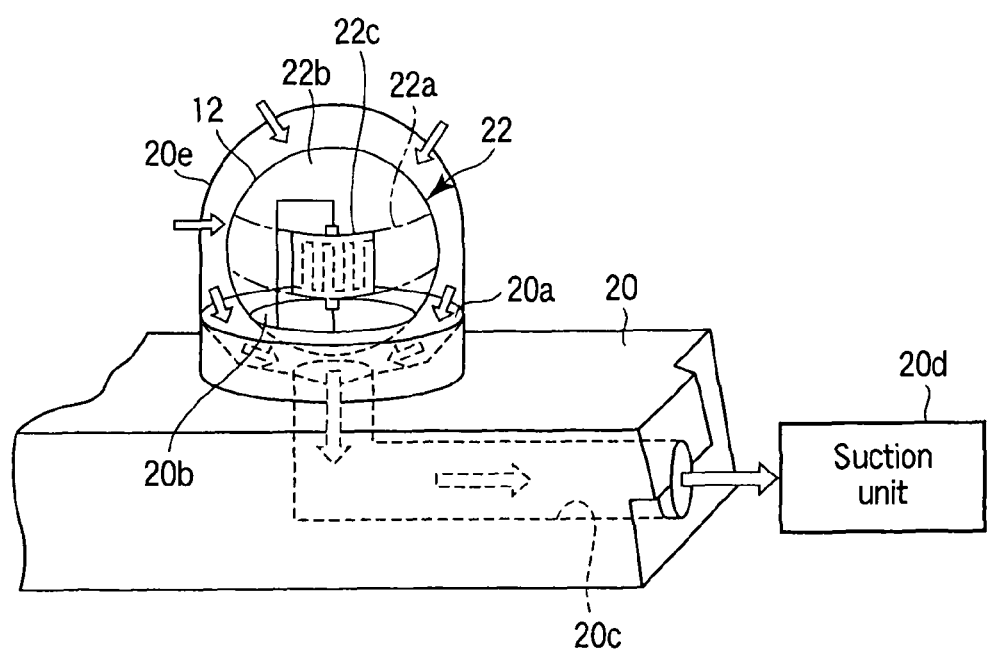
FIG. 2 is an enlarged perspective view schematically showing one of a plurality of gas detectors in a gas detection part of the gas concentration distribution measuring apparatus in FIG. 1.

The gas detector 12 includes, as shown in FIG. 2 in an enlarged manner, a surface acoustic wave element 22 including at least one surface acoustic wave circulating path 22a which is circularly continuous with a portion of a spherical shape and along which a surface acoustic wave can be propagated.

Such a surface acoustic wave element 22 is well known. The surface acoustic wave element 22 includes a base member 22b which is configured to allow a surface acoustic wave to be excited along the surface thereof and to allow the excited surface acoustic wave to be propagated along the surface in a predetermined direction. The base member 22b can be formed by a combination of a main body, the main body being formed from a material along which a surface acoustic wave can not be excited and the surface acoustic wave can not be propagated in a shape (for example, a spherical shape or barrel shape) including a surface region of a portion of a spherical shape which is circularly continuous, and a layer formed by attaching a surface acoustic wave excitable and propagatable material (for example, a piezoelectric material) to the surface region of the main body. Alternatively, the base member 22b can be formed by the surface acoustic wave excitable and propagatable material (for example, crystal and langasite) in the shape (for example, the spherical shape or barrel shape) including the surface region by the portion of the spherical shape or barrel shape) which is circularly continuous.

Currently, the base member 22b having the surface region in which a curved surface of about 3 mm in diameter can be used.

It is known that, when crystal or langasite is formed into the shape having the surface region which is circularly continuous with the portion of the spherical shape (for example, a spherical shape or barrel shape), the crystal or langasite is formed to extend its crystal plane along the surface region so that a surface acoustic wave can be propagated very well along a line where the crystal plane is exposed in the surface region.

A surface acoustic wave exciting element, a unit of comb-shaped electrodes 22c in this embodiment, is placed on the surface acoustic wave circulating path 22a. By applying a high-frequency burst current to the unit of comb-shaped electrodes 22c, surface acoustic waves are excited along the surface acoustic wave circulating path 22. And, the surface acoustic waves propagate in a direction perpendicular to a plurality of branches of the comb-shaped electrode 22c. The unit of comb-shaped electrodes 22c receives the surface acoustic waves circulating along the surface acoustic wave circulating path 22a and generates a signal voltage corresponding to the strength of the received surface acoustic waves. That is, the unit of comb-shaped electrodes 22c also functions as a surface acoustic wave receiving element.

The unit of comb-shaped electrodes 22c is connected to a publicly known surface acoustic wave element control part (not shown) accommodated in the outer housing of the gas concentration distribution display unit 18 by electric wires (not shown) extending along the surface of the supporting member 20 or in the supporting member 20 toward the outer housing. The publicly known surface acoustic wave element control part (not shown) includes a publicly known high-frequency power supply (not shown), which supplies a high-frequency current to the unit of comb-shaped electrodes 22$c$ for exciting surface acoustic waves in burst form, and a signal receiving circuit (not shown) for receiving a signal voltage generated by the unit of comb-shaped electrodes 22$c$, the signal voltage being in accordance with strength of the surface acoustic waves received by the unit of comb-shaped electrodes 22$c$.

Surface acoustic waves excited and propagated in a predetermined direction along a surface along which surface acoustic waves can be excited and propagated, diffuse gradually in a direction perpendicular to the direction of their propagation and loses strength thereof while the surface acoustic waves are propagated.

However, it is known that, when surface acoustic waves are excited and propagated along a surface region which circularly continuous with a portion of a spherical shape and along which surface acoustic waves can be excited and propagated in a direction circularly continuous, the surface acoustic waves can be propagated in a direction, in which the surface region is circularly continuous, without being diffused in a direction perpendicular to the direction of their propagation by setting the frequency of the surface acoustic waves, a width of the surface acoustic waves in the direction perpendicular to the direction in which the surface region is circularly continuous, etc. to satisfy predetermined conditions (for example, see K. Yamanaka, S. Ishikawa, N. Nakaso, N. Takada, D. Y. Sim, T. Mihara, A. Mizukami, I. Satoh, S. Akao and Y. Tsukahara, "Ultramultiple roundtrips of surface acoustic wave on sphere realizing innovation of gas sensors", IEEE Trans. UFFC, 53 (2006), pp. 793-801).

Since the surface acoustic waves propagating in the circularly continuing direction along the surface region does not diffuse in the direction perpendicular to the direction of their propagation, the surface acoustic waves theoretically can circulate repeatedly and infinitely in the circularly continuing direction along the surface region while maintaining their strength.

Nevertheless, the surface acoustic waves propagating in the circularly continuing direction along the surface region change their speed (that is, a time needed for one roundtrip) and strength when an environment in which the surface acoustic wave propagates. Particularly, when some substance adheres on the surface region, the adhered substance significantly changes the speed and strength of the surface acoustic waves propagating in the surface region, due to its mass effect in accordance with amount of the adhered substance.

Therefore, by comparing the speed and/or strength of the surface acoustic waves propagating in the surface region before the environment changes and that or those of the surface acoustic waves propagating in the surface region after the environment changes, the degree of change in the environment can be known. The surface acoustic waves propagating in the surface region can be picked up by a surface acoustic wave excitation element, the unit of comb-shaped electrodes 22$c$ in this embodiment.

With increasing a distance in which the surface acoustic waves propagate along the surface region (in this embodiment, the number of circulating times of the surface acoustic waves along the surface acoustic wave circulating path 22$a$), the above described change is enlarged so that the change can be measured more clearly, that is, more accurately.

For example, if only the concentration of a predetermined gas in the environment changes, the change of the environment means the change of the concentration of the predetermined gas.

If only the change in concentration of a predetermined gas in the environment should be measured more accurately and efficiently, a gas sensitive layer that is sensitive to only the predetermined gas is provided at least on a portion of the surface region. Such a gas sensitive layer can be formed, for example, from a material that absorbs or adsorbs only the predetermined gas and, for example, a palladium-nickel alloy is known to adsorb a hydrogen gas well.

The surface acoustic wave as described herein includes all elastic waves that propagate with concentrated energy on or adjacent to the surface of a solid. As the elastic waves, for example, a Rayleigh wave, a Sezawa wave that propagates while leaking a small amount of energy to the solid, an SH wave, a Love wave that propagates only in a film which is provided on the surface of the solid and in which a surface acoustic wave can propagate, and a corridor wave are known.

The surface acoustic wave element 22 is supported at its region other than the surface acoustic wave circulating path 22$a$ along which surface acoustic waves propagate to a predetermined position on the surface of the supporting member 20 by a publicly known supporting means such as an adhesive.

More specifically, in this embodiment, a seat member 20$a$ is fixed to a predetermined position on the surface of the supporting member 20 and an indent 20$b$ is formed in the seat member 20$a$. And, a portion of a region excluding the surface acoustic wave circulating path 22$a$ on the surface acoustic wave element 22 is seated on the indent 20$b$. A vent hole 20$c$ is formed in the supporting member 20 to extend from the dent 20$b$ to the outer housing of the gas concentration distribution display unit 18 in the supporting member 20, and an extending end of the vent hole 20$c$ is connected to a publicly known suction unit 20$d$ accommodated in the outer housing.

A filter 20$e$ covering the surface acoustic wave element 22 seated on the dent 20$b$ is further provided on the seat member 20$a$. The filter 20$e$ is formed from a gas transmissible material (for example, a porous material) to prevent foreign matter excluding gases, for example, a solid material, from coming into contact with the surface acoustic wave circulating path 22$a$ of the surface acoustic wave element 22.

For example, a filter manufactured by Nippon Seisen Co., Ltd. and marketed under the trade name of NASclean can be used as the filter 20$e$. This filter is a metal membrane filter obtained by sintering laminated fine stainless steel short fibers (1 μm in diameter) and can completely remove particles of 0.03 μm or more while maintaining permeability of gas.

The publicly known suction unit 20$d$ can exchange a gas in a space enclosed by the filter 20$e$ over the seat member 20$a$ for a gas surrounding the filter 20$e$ through the vent hole 20$c$ within two seconds. That is, the publicly known suction unit 20$d$ provides a gas exchange element in cooperation with the vent hole 20$c$.

In order to measure only the change in concentration of the predetermined gas in the environment more efficiently and accurately, it is only necessary to provide a gas sensitive layer that is sensitive to only the predetermined gas at least on a portion of the surface region, as described above. But, alternatively, the surface acoustic wave element 22 may be covered with a filter which can pass only the predetermined gas. For example, Japanese Patent Application KOKAI Publication No. 2007-271577 discloses a filter that passes only a hydrogen gas.

Next, a typical method of using the gas concentration distribution measuring apparatus 10 configured as described above and according to the first embodiment of the present invention will be described with reference to FIGS. 3 and 4.

The gas concentration distribution measuring apparatus 10 can measure a concentration distribution of one type of gas while the concentration distribution of the only one type of gas in a desired space is not uniform.

Figure 3:
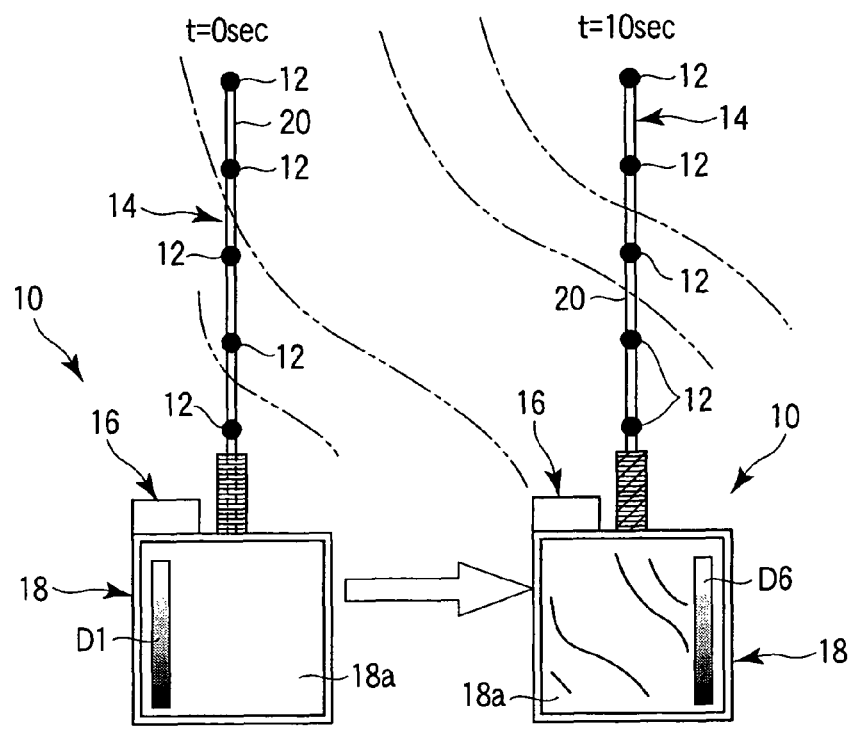
FIG. 3 is a plan view schematically showing a first method for measuring a concentration distribution of a predetermined gas in a predetermined space by using the gas concentration distribution measuring apparatus in FIG. 1.

The gas concentration distribution measuring apparatus 10 is held at a gas measurement start position (initial position) in the desired space, as shown on the left side in FIG. 3, to measure the concentration of gas at a plurality of positions where the plurality of the gas detectors 12 are arranged in the desired space by using the plurality of gas detectors 12. A signal voltage generated by each of the plurality of gas detectors 12 in accordance with the concentration of gas is transmitted to the signal receiving circuit of the publicly known surface acoustic wave element control part (not shown) described above and accommodated in the outer housing of the gas concentration distribution display unit 18.

These signal voltages (that is, measured values of the gas concentration) and position informations (initial positions shown on the left side in FIG. 3) of the plurality of gas detectors 12 measured by the gas detector position information measuring part 16 when the plurality of gas detectors 12 finishes the measurement of the gas concentration, are inputted to the gas concentration distribution display unit 18, the gas concentration distribution display unit 18 displays a linear distribution D1 of the concentration of the predetermined gas in two dimensions at the initial positions shown on the left side in FIG. 3, on the display device 18a, based on the measured values of the gas concentration and position information of these gas detectors 12.

Next, the gas concentration distribution measuring apparatus 10 is moved linearly and horizontally from the initial position shown on the left side in FIG. 3 to the end position shown on the right side in FIG. 3. When there is no blower such as an air conditioner and a fan, air in a room moves at 0.2 m/s or less. Therefore, if the moving distance from the initial position to the end position is 2 m, the gas concentration distribution measuring apparatus 10 is moved in 10 seconds (2 m/0.2 m/s=10 seconds) or less and if each of the plurality of gas detectors 12 can measure the gas concentration at least at four positions between the initial position and the end position, in addition to the initial position and the end position, a rough distribution of the gas concentration (a striped pattern shown by two-dots chain lines in FIG. 3) in a rectangular horizontal space region from the initial position shown on the left side in FIG. 3 to the end position shown on the right side in FIG. 3 scanned by the supporting member 20 of the gas detection part 14 can be obtained.

In order to make each of the plurality of gas detectors 12 measure the gas concentration at least at the four positions in 10 seconds as described above, each of the gas detectors 12 should be able to measure the gas concentration within two seconds per position of at least at the four positions. And, to measure the gas concentration precisely within such a time limit is possible by configuring each of the gas detectors 12 with the surface acoustic wave element 22. Further, if, as shown in FIG. 2, the surface acoustic wave element 22 of each of the gas detectors 12 is covered with the filter 20e, the surface acoustic wave element 22 of each of the gas detectors 12 can precisely measure the concentration of a gas adjacent to the outer side of the filter 20e within the time limit because the publicly known suction unit 20d can exchange the gas in the space enclosed by the filter 20e over the seat member 20a for the gas surrounding the filter 20e through the vent hole 20c within two seconds.

The gas concentration distribution display unit 18 can display the linear distribution of gas concentration measured by the plurality of gas detectors 12 each time the gas detectors 12 measure the gas concentration at each of the at least four positions between the initial position and the end position, in addition to the initial position and the end position while the gas concentration distribution measuring apparatus 10 is moved, for example, as indicated by a reference numeral D1 on the display device 18a of the gas concentration distribution display unit 18 in the initial position shown on the left side in FIG. 3 or as indicated by a reference numeral D6 on the display device 18a of the gas concentration distribution display unit 18 in the end position shown on the right side in FIG. 3.

Further, based on the linear gas concentration distributions D1 to D6 measured by each of the plurality of gas detectors 12 at each of the plurality of positions ranging from the initial position to the end position, the gas concentration distribution display unit 18 can display as illustrated by a solid striped pattern in a rectangular region of the display device 18a of the gas concentration distribution display unit 18 of the gas concentration distribution measuring apparatus 10 at the end position shown on the right side in FIG. 3, the solid striped pattern corresponding to the actual rough distribution of gas concentration illustrated as the striped pattern of two-dots chain lines in a rectangular horizontal space region scanned by the supporting member 20 of the gas detection part 14 from the initial position shown on the left side in FIG. 3 to the end position shown on the right side in FIG. 3.

The gas concentration distribution display unit 18 can know the positions relative to the initial position of the plurality of gas detectors 12 while it is moving, by the gas detector position information measuring part 16.

Figure 4:
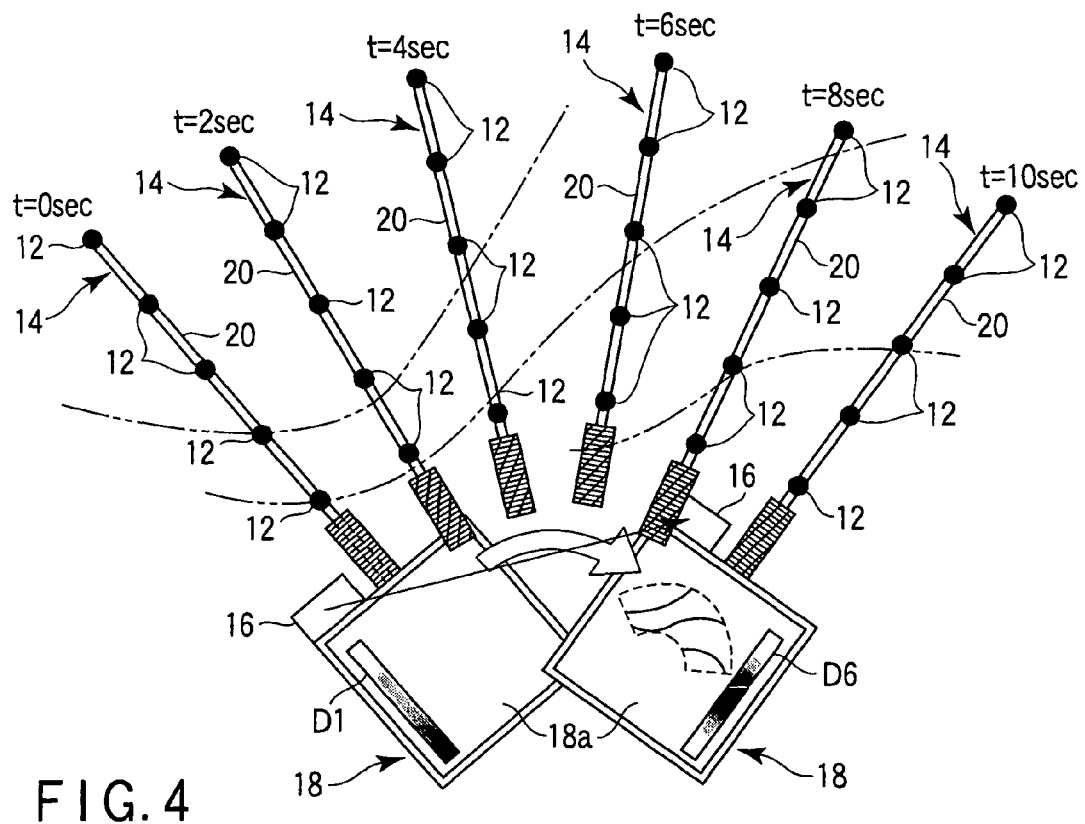
FIG. 4 is a plan view schematically showing a second method for measuring the concentration distribution of the predetermined gas in the predetermined space by using the gas concentration distribution measuring apparatus in FIG. 1.

FIG. 4 shows another typical method of using the gas concentration distribution measuring apparatus 10 configured as described above and according to the first embodiment of the present invention.

FIG. 4 shows that, while the gas concentration distribution measuring apparatus 10 arranged at a gas concentration measuring start position (initial position at the left end in FIG. 4) is moved to a gas concentration measuring end position (end position at the right end in FIG. 4) at which the tip of the supporting member 20 supporting the plurality of gas detectors 12 is 2 m away from that of the supporting member 20 of the initial position around the gas concentration distribution display unit 18 in the clockwise direction, each of the plurality of gas detectors 12 on the supporting member 20 performs a measurement of gas concentration at least at four positions.

As a result, a rough distribution of gas concentration (a striped pattern shown by two-dots chain lines in FIG. 4) in a fan-shaped horizontal region scanned by the supporting member 20 of the gas detection part 14 from the initial position shown on the left side in FIG. 4 to the end position shown on the right side in FIG. 4 can be obtained.

Then, based on the linear gas concentration distributions D1 to D6 each of which is measured by the plurality of gas detectors 12 at each of the plurality of positions ranging from the initial position to the end position, the gas concentration distribution display unit 18 can display the rough distribution of gas concentration as illustrated by a solid striped pattern in a fan-shaped region of the display device 18a of the gas concentration distribution display unit 18 of the gas concentration distribution measuring apparatus 10 at the end position shown at the right end in FIG. 4, the rough distribution of the gas concentration illustrated by the solid striped pattern being corresponding to the actual rough distribution of gas concentration illustrated by two-dots chain lines in a striped pattern in a fan-shaped horizontal region scanned by the base 20 of the gas detection part 14 from the initial position shown at the left end in FIG. 4 to the end position shown at the right end in FIG. 4.

In the two typical using methods illustrated in FIGS. 3 and 4, the supporting member 20 of the gas detection part 14 scans horizontally in a rectangular shape or in a fan shape from the initial position to the end position, the plurality of gas detectors 12 on the supporting member 20 measures the concentration distribution of gas in the rectangular or fan-shaped two dimensional region in the horizontal direction, and measurement results are displayed on the display device 18a of the gas concentration distribution display unit 18. However, by moving the supporting member 20 of the gas detection part 14 in a vertical direction or in an oblique direction, the concentration distribution of gas in a rectangular or fan-shaped two dimensional region in the vertical direction or in the oblique direction can also be measured and their measurement results can be displayed on the display device 18a of the gas concentration distribution display unit 18.

[First Modification of the Gas Detector]

In the gas concentration distribution measuring apparatus 10 according to the first embodiment described above, one surface acoustic wave element 22 is used as the gas detector 12. As described above, the surface acoustic wave element 22 can precisely measure a change in the environment surrounding the surface acoustic wave element 22. However, this prevents the surface acoustic wave element 22 from measuring the gas concentration more precisely.

That is, a slight change in an elasticity of the base member 22b of the surface acoustic wave element 22 due to a change in temperature of a surrounding environment or a change in a pressure in the surrounding environment causes a change in vibrations of the surface acoustic waves propagating along the surface acoustic wave circulating path 22a of the base member 22b of the surface acoustic wave element 22. Then, such changes fluctuate the time needed for a surface acoustic wave to propagate along the whole surface acoustic wave circulating path 22a of the base member 22b of the surface acoustic wave element 22 (one-circulating time of the surface acoustic wave). This means that even if a gas of the same concentration is measured by the surface acoustic wave element 22, slightly different measurement results are obtained when the temperature or pressure around the surface acoustic wave element 22 is changed.

Therefore, in order to measure the concentration of a gas more precisely by using the surface acoustic wave element 22, it is necessary, as described above, to remove fluctuations of the one-circulating time caused by fluctuations in temperature or pressure around the surface acoustic wave element 22, from the desired one-circulating time of the surface acoustic wave corresponding to the gas concentration on the surface acoustic wave element 22.

A gas detector 12' according to the first modification for this purpose is shown in FIG. 5.

In the gas detector 12' according to the first modification, one side surface of a barrel-shaped base member 22'b of a first surface acoustic wave element 22' is seated in the dent 20b of the seat member 20a fixed to the predetermined position of the supporting member 20, and further one side surface of a barrel-shaped base member 22"b of a second surface acoustic wave element 22" is fixed to the other side surface of the barrel-shaped base member 22'b of the first surface acoustic wave element 22'. The dimensions of the barrel-shaped base member 22'b of the first surface acoustic wave element 22' and those of the barrel-shaped base member 22"b of the second surface acoustic wave element 22" are identical with each other. Further, a gas sensitive layer sensitive to only a predetermined gas is provided, in addition to the unit of comb-shaped electrodes 22c, on at least a portion of the surface acoustic wave circulating path 22a of one of the first surface acoustic wave element 22' and the second surface acoustic wave element 22", and nothing is provided, except the unit of comb-shaped electrodes 22c, on the surface acoustic wave circulating path 22a on the other.

The first surface acoustic wave element 22' and the second surface acoustic wave element 22" on the seat member 20a are covered with a cover 20f having the above described filter 20e. The cover 20f protects the first surface acoustic wave element 22' and second surface acoustic wave element 22" on the seat member 20a from damage due to external force.

In the gas detector 12' according to the first modification and configured as described above, the same high-frequency signal in burst form is applied to each of the unit of comb-shaped electrodes 22c of the first surface acoustic wave element 22' and that of the second surface acoustic wave element 22", and surface acoustic waves of the same strength are excited and propagated along each of the first surface acoustic wave element 22' and the second surface acoustic wave element 22".

Then, the surface acoustic waves are picked up by the unit of comb-shaped electrodes 22c after the surface acoustic waves circulate around the surface acoustic wave circulating path 22a on each of the first surface acoustic wave element 22' and the second surface acoustic wave element 22" a predetermined number of times, and then the phases or strength at a predetermined time after circulating many times or delay times needed for the predetermined number of circulation about the surface acoustic waves picked up from the first and second surface acoustic wave elements 22' and 22" are compared from each other. After that, the receiving strength or delay time of the surface acoustic waves picked up as described above by the unit of comb-shaped electrodes 22c of the surface acoustic wave circulating path 22a without the gas sensitive layer sensitive to the predetermined gas on the other of the first surface acoustic wave element 22' and the second surface acoustic wave element 22" is subtracted from the receiving strength or delay time of the surface acoustic waves picked up as described above by the unit of comb-shaped electrodes 22c on the surface acoustic wave circulating path 22a provided with the gas sensitive layer sensitive to the predetermined gas at least at the portion of the surface acoustic wave circulating path 22a of one of the first surface acoustic wave element 22' and the second surface acoustic wave element 22", so that the difference is a measured value more exactly corresponding to the concentration of the predetermined gas.

Further in this modification, at least one surface acoustic wave element (not shown) having the same configuration and dimensions as those of each of the first surface acoustic wave element 22' and the second surface acoustic wave element 22" may further be stacked on the second surface acoustic wave element 22" in the cover 20f and a gas sensitive layer sensitive to only a gas different from the predetermined gas may be provided on a portion of a surface acoustic wave circulating path of the further stacked at least one surface acoustic wave element (not shown).

[Second Modification of the Gas Detector]

As shown in FIG. 6, in a gas detector 12" according to a second modification, one spherical surface acoustic wave element 22''' is seated on the dent 20*b* of the seat member 20*a* fixed to the predetermined position of the supporting member 20.

A base member 22'''*b* of the surface acoustic wave element 22''' is formed from a material on which surface acoustic waves can be excited, and includes a plurality of surface acoustic wave circulating paths 22'*a* on the surface thereof. Each surface acoustic wave circulating path 22'*a* is a portion of a spherical shape and circularly continuous, and the surface acoustic waves can propagate along the circulating path 22'*a*. As such a base member, for example, lithium niobate and lithium tantalite are well known. A material that absorbs or adsorbs a predetermined gas, in addition to the unit of comb-shaped electrodes 22*c*, is provided on one among the plurality of surface acoustic wave circulating paths 22'*a*, and only the unit of comb-shaped electrodes 22*c* is provided on the other one of the surface acoustic wave circulating paths 22'*a*.

The gas detector 12" according to the second modification described above can perform the same function as that of the gas detector 12' according to the first modification described with reference to FIG. 5, that is, each of the gas detectors 12" and 12' can remove the influence caused by fluctuations in temperature or pressure from results of gas concentration measurement. Besides, since the gas detector 12" according to the second modification uses only one spherical surface acoustic wave element 22''', the gas detector 12" has a simpler configuration and is easier to manufacture and assemble and also has smaller outside dimensions in comparison with the gas detector 12' described with reference to FIG. 5 and according to the first modification that needs the two barrel-shaped surface acoustic wave elements 22' and 22".

In the gas detector 12" according to the second modification and using only one surface acoustic wave element 22''' using the base member 22'''*b* including the plurality of the surface acoustic wave circulating paths 22'*a*, it becomes possible to measure concentrations of mutually different gases by providing gas sensitive layers being sensitive to mutually different gases on the plurality of the surface acoustic wave circulating paths 22'*a*. Further, by applying a high-frequency signal in burst form to the surface acoustic wave circulating path 22'*a* having no gas sensitive layer, like the plurality of surface acoustic wave circulating paths 22'*a* provided with the gas sensitive layers being sensitive to the mutually different gases, simultaneously in the same strength at the same frequency, and by picking up the surface acoustic waves excited and propagated along the surface acoustic wave circulating paths 22'*a* with the high-frequency signal in the same circulation count, and by comparing and calibrating measurement results with each other as described above, an influence of fluctuations in temperature or pressure is removed from the measured concentrations of the mutually different gases so that values of the measured concentrations of the mutually different gases can be more precisely.

Also in the gas detector 12" according to the second modification shown in FIG. 6, the surface acoustic wave element 22''' seated on the dent 20*b* of the seat member 20*a* fixed to the predetermined position of the supporting member 20 is covered with the cover 20*f* having the filter 20*e*.

In each of the gas concentration distribution measuring apparatuses 10 according to the first embodiment and the first and second modifications, the plurality of gas detectors 12, 12' or 12" are arranged at mutually different positions on the rod shaped supporting member 20 and the plurality of positions corresponding to the plurality of gas detectors 12, 12' or 12" on the base 20 are communicated with the suction unit 20*d* by the vent hole 20*c* in order to reduce the time needed to exchange the gas in the space enclosed by the filter 20*e* covering the gas detectors 12, 12' or 12".

Instead of the configuration described above, it may be possible to remove the plurality of gas detectors 12, 12' or 12" from the above mutually different positions on the rod shaped supporting member 20, and to provide a plurality of the vent holes 20*c* in the supporting member 20 so that the plurality of the vent holes 20*c* extend from the mutually different positions on the supporting member 20 to the outer housing of the gas concentration distribution display unit 18, and to arrange the plurality of gas detectors 12, 12' or 12" at positions in the plurality of the vent holes 20*c* before the suction unit 20*d*. In this case, it is necessary to consider the time needed for a gas sucked by the suction unit 20*d* through the vent holes 20*c* from the mutually different positions of the supporting member 20 to reach the gas detectors 12, 12' or 12" arranged in the vent holes 20*c* inside the outer housing of the gas concentration distribution display unit 18, when creating a gas concentration distribution. However, since the surface acoustic wave elements 22, 22', 22", or 22''' of the gas detectors 12, 12' or 12" can be arranged closer to the surface acoustic wave element control part accommodated in the outer housing, the surface acoustic wave element control part can control operations of the surface acoustic wave elements 22, 22', 22", or 22''' of the gas detectors 12, 12' or 12" more precisely, and temperature management and maintenance for the surface acoustic wave elements 22, 22', 22", or 22''' can be more easier.

Second Embodiment

A gas concentration distribution measuring apparatus 30 according to a second embodiment of the present invention will be described with reference to FIG. 7.

The gas concentration distribution measuring apparatus 30 includes a gas detection part 34, a gas detector position information measuring part 36, and a gas concentration distribution display unit 38. The gas detection part 34 includes gas detectors 32*a*, 32*b*, 32*c*, 32*d*, and 32*e*, each of which measures a concentration of a predetermined gas within two seconds at a plurality of mutually different positions. The gas detector position information measuring part 36 measures, in addition to position information of the plurality of gas detectors 32*a*, 32*b*, 32*c*, 32*d*, and 32*e* in directions (X direction, Y direction) being in parallel to the surface of FIG. 7, position information thereof in a direction (Z direction) perpendicular to the surface of FIG. 7. And, the gas concentration distribution display unit 38 is inputted with values of gas concentrations measured by the plurality of gas detectors 32*a*, 32*b*, 32*c*, 32*d*, and 32*e* of the gas detection part 34 and position information of the plurality of gas detectors 32*a*, 32*b*, 32*c*, 32*d*, and 32*e* measured by the gas detector position information measuring part 36 when the plurality of gas detectors 32*a*, 32*b*, 32*c*, 32*d*, and 32*e* finish measurement of gas concentrations, and then the gas concentration distribution display unit 38 displays a distribution of concentrations of the predetermined gas in three dimensions based on the measured values of the gas concentrations and the position information of the gas detectors 32*a*, 32*b*, 32*c*, 32*d*, and 32*e*.

Figure 7:
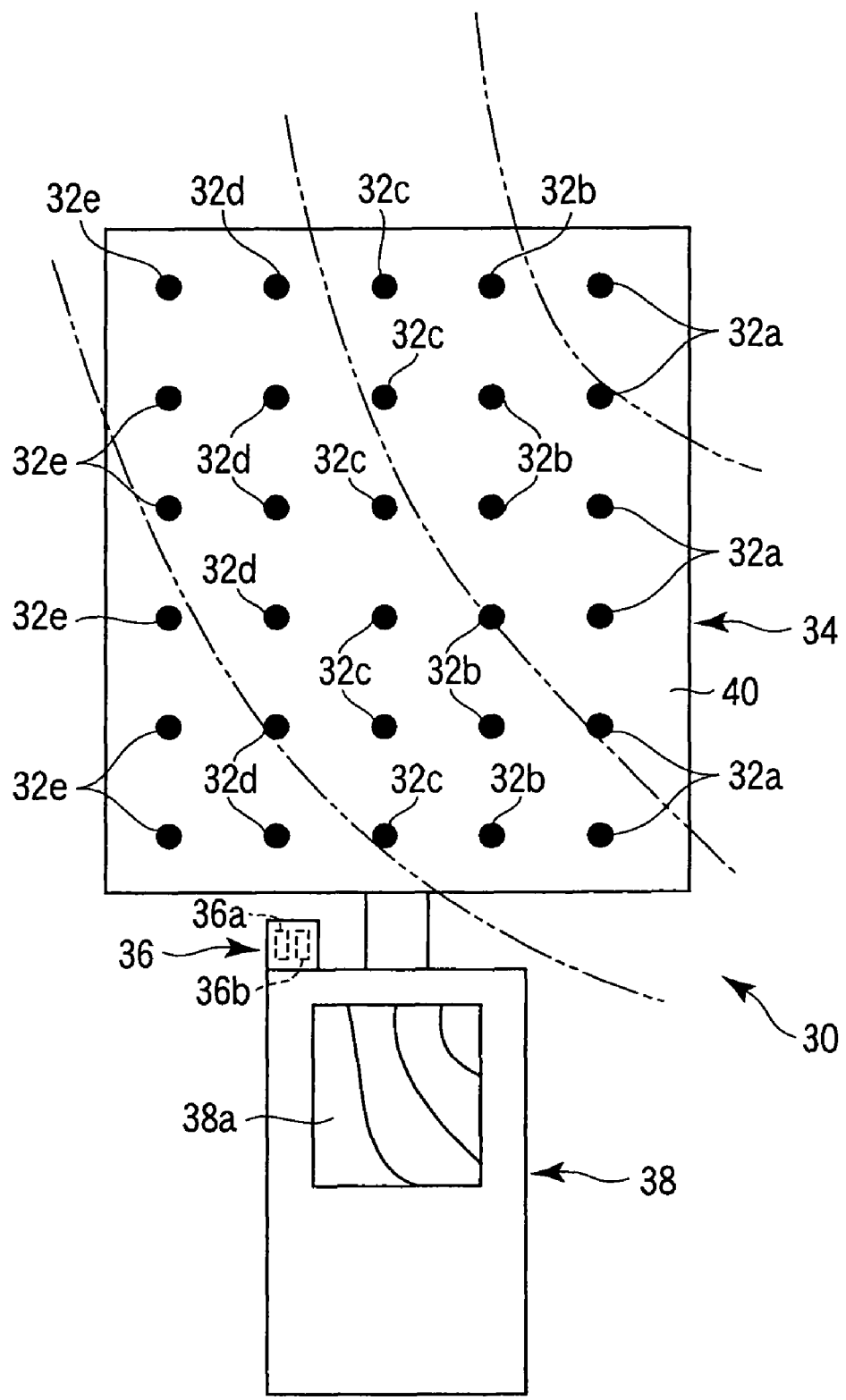
FIG. 7 is a schematic front view of the whole of a gas concentration distribution measuring apparatus according to a second embodiment of the present invention.

In this embodiment, the plurality of gas detectors 32*a*, 32*b*, 32*c*, 32*d*, or 32*e* of the same type are arranged in the vertical direction in FIG. 7 mutually at equal intervals on a flat-plate-like supporting member 40 to constitute a column, and also the plurality of gas detectors 32*a*, 32*b*, 32*c*, 32*d*, and 32*e* of the different type are arranged in the horizontal direction in FIG. 7 mutually at equal intervals to constitute a row.

Each of the gas detectors 32a, 32b, 32c, 32d, and 32e is configured, like, for example, the gas detector 12 in FIG. 2, by a surface acoustic wave element (not shown).

A portion of the plate-like supporting member 40 of the gas detector 34 is fixed to a predetermined position of the outer housing of the gas concentration distribution display unit 38. The gas detector position information measuring part 36 is also fixed to the outer housing of the gas concentration distribution display unit 38. The gas concentration distribution display unit 38 includes a display device 38a exposed in the outer surface of the outer housing, and the display device 38a is a liquid crystal display device in this embodiment.

The gas detector position information measuring part 36 includes at least one of a publicly known acceleration sensor and angular velocity sensor. In this embodiment, the gas detector position information measuring part 36 includes both the publicly known acceleration sensor 36a and angular velocity sensor 36b. Each of the acceleration sensor 36a and the angular velocity sensor 36b is operable at least in two directions of the X and Y directions and, further operable in three directions by adding the Z direction.

The gas concentration distribution measuring apparatus 30 configured as described above and according to the second embodiment of the present invention is used in the same manner as the gas concentration distribution measuring apparatus 10 according to the first embodiment of the present invention and described with reference to FIGS. 1 to 4.

The function of the gas concentration distribution measuring apparatus 30 is different from that of the gas concentration distribution measuring apparatus 10 in that measurement and display of a gas concentration distribution in three-dimensional space are performed by moving the gas detectors 32a, 32b, 32c, 32d, and 32e arranged two-dimensionally in the vertical direction.

[High-Speed Measuring Method of the Concentration of a Predetermined Gas by the Plurality of Gas Detectors of the Gas Detection Part]

In the gas concentration distribution measuring apparatus 10 according to the first embodiment of the present invention described with reference to FIGS. 1 to 4, it is preferable that the time necessary for all the plurality of gas detectors 12 of the gas detection part 14 supported on the supporting member 20 to measure the concentration of a predetermined gas at one movement position of the supporting member 20 is as shorter as possible.

This is because the number of movement positions at which all the plurality of gas detectors 12 of the supporting member 20 can measure the concentration of a predetermined gas between the initial position where measurement of the concentration of the predetermined gas is started in a predetermined space and the end position where measurement of the concentration of the predetermined gas is finished can be increased, and also all the plurality of gas detectors 12 of the supporting member 20 can measure the concentration of the predetermined gas repeatedly at one movement position. In the former case, the concentration distribution of the predetermined gas in a two-dimensions scanned by the supporting member 20 can be measured more finely. In the latter case, accuracy of measured values of the concentration of the predetermined gas in the two-dimensions scanned by the supporting member 20 can be improved. Further, it is preferable that the concentration distribution of the predetermined gas is displayed on the display device 18a in real time with movement of the supporting member 20.

The same things are applied to the gas concentration distribution measuring apparatus 30 according to the second embodiment of the present invention and described with reference to FIG. 7.

Normally, the plurality of gas detectors 12 of the supporting member 20 are caused to measure the gas concentration one by one at one measurement position by the publicly known surface acoustic wave element control part (not shown) accommodated in the outer housing of the gas concentration distribution display unit 18. This makes the configuration of the publicly known surface acoustic wave element control part (not shown) be simpler so as to lower manufacturing costs of the gas concentration distribution measuring apparatus 10 according to the first embodiment of the present invention, and makes outside dimensions of the gas concentration distribution measuring apparatus 10 and the weight thereof being as smaller as possible, and makes power needed to drive the gas concentration distribution measuring apparatus 10 decrease so as to make the capacity of the power supply for the gas concentration distribution measuring apparatus 10 being smaller and to improve a portability of the gas concentration distribution measuring apparatus 10.

Nonetheless, by the conventional method for measuring the concentration of a predetermined gas in which the plurality of gas detectors 12 of the supporting member 20 measure the gas concentration one by one at one measurement position, there is a limit to reduce the time necessary for all the plurality of gas detectors 12 supported on the supporting member 20 of the gas detection part 14 to measure the concentration of the predetermined gas at one movement position of the base 20.

Figure 9:
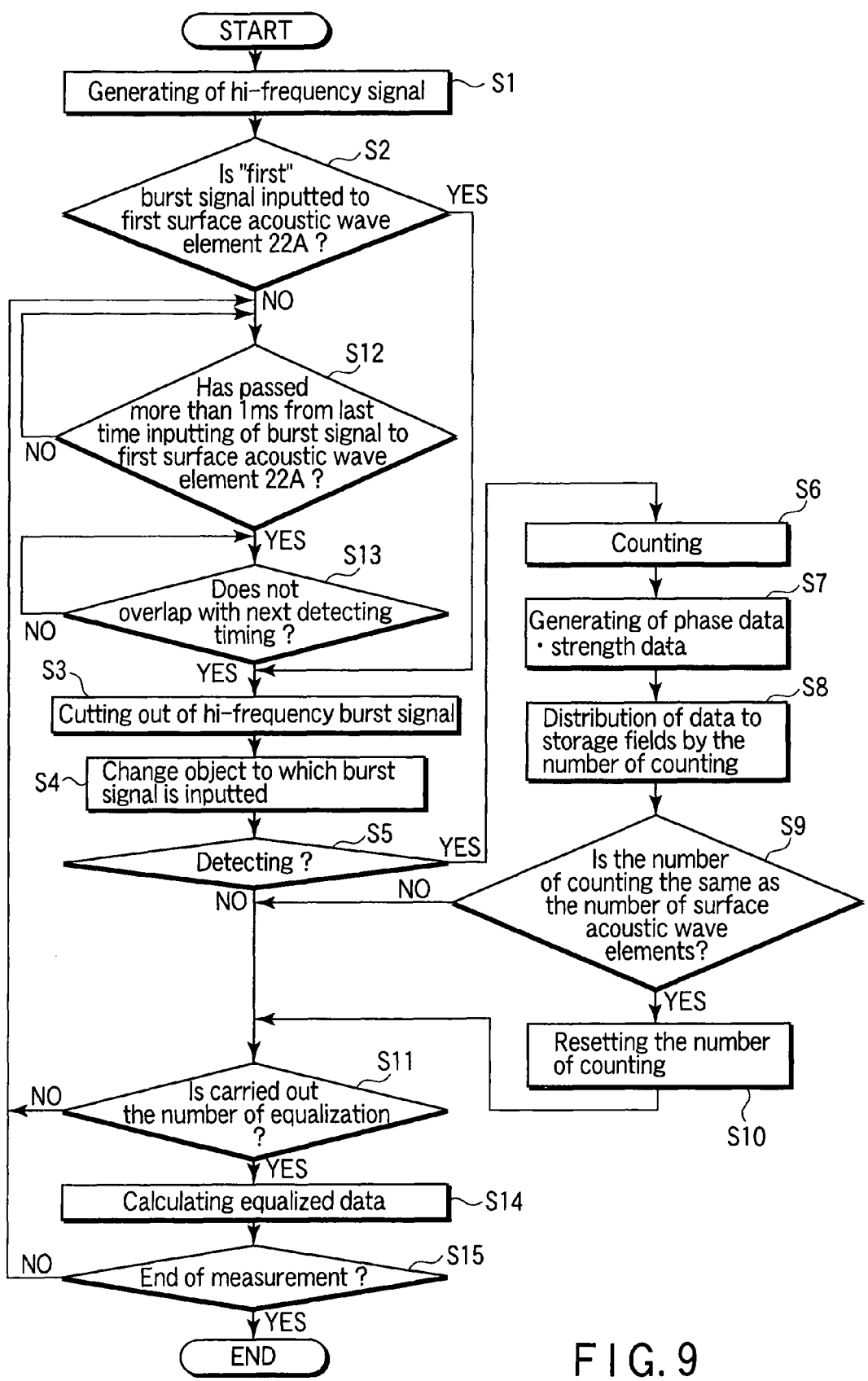
FIG. 9 is a schematic flow chart showing an operation of the gas detection part controlled by the surface acoustic wave element control part in FIG. 8.
Figure 10:
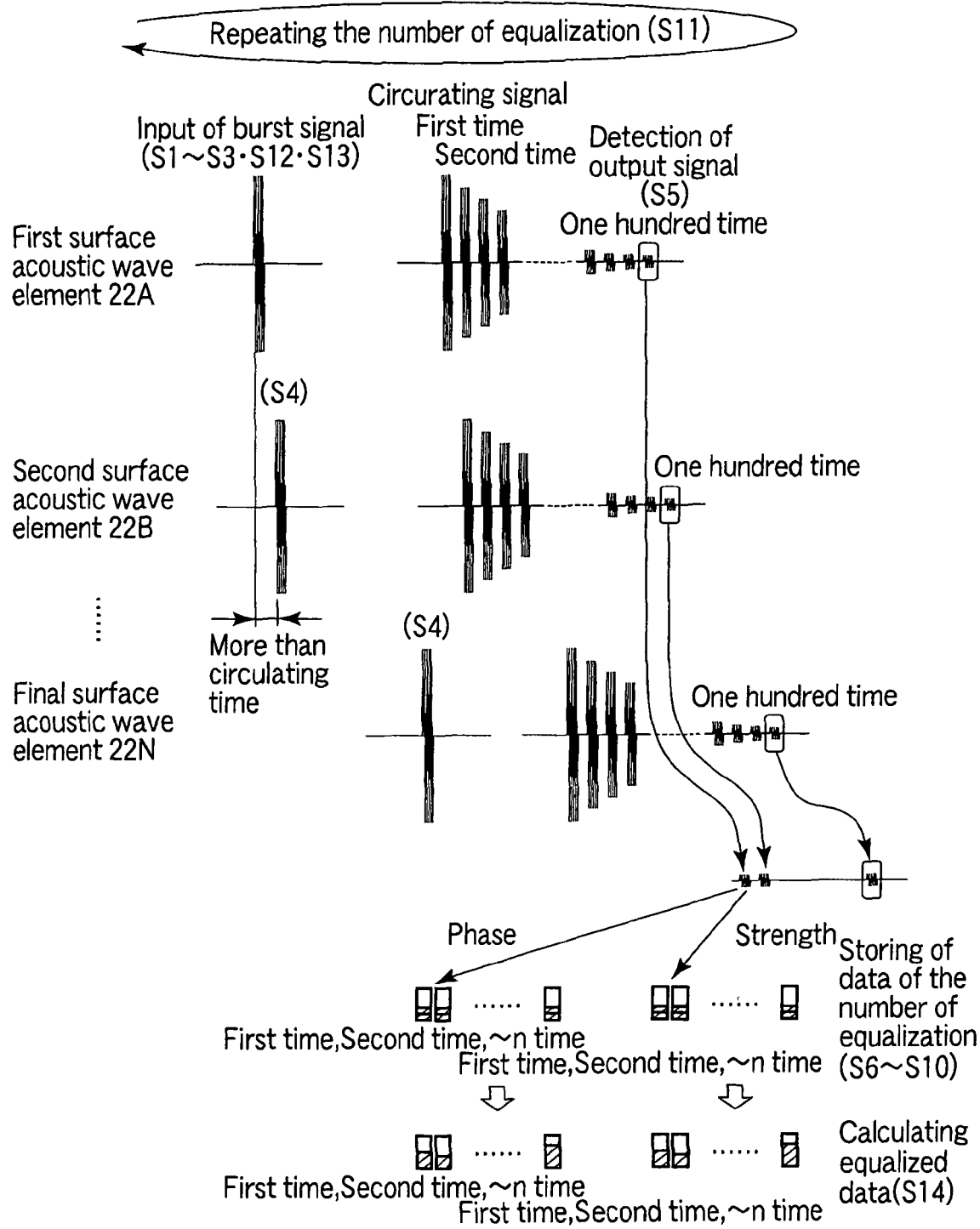
FIG. 10 is a signal correlation diagram schematically showing a correlation between signals in the flow chart in FIG. 9.

Next, a method for measuring the concentration of a predetermined gas by the plurality of gas detectors 12 of the gas detection part 14 at higher speed will be described with reference to FIGS. 8 to 10.

Figure 8:
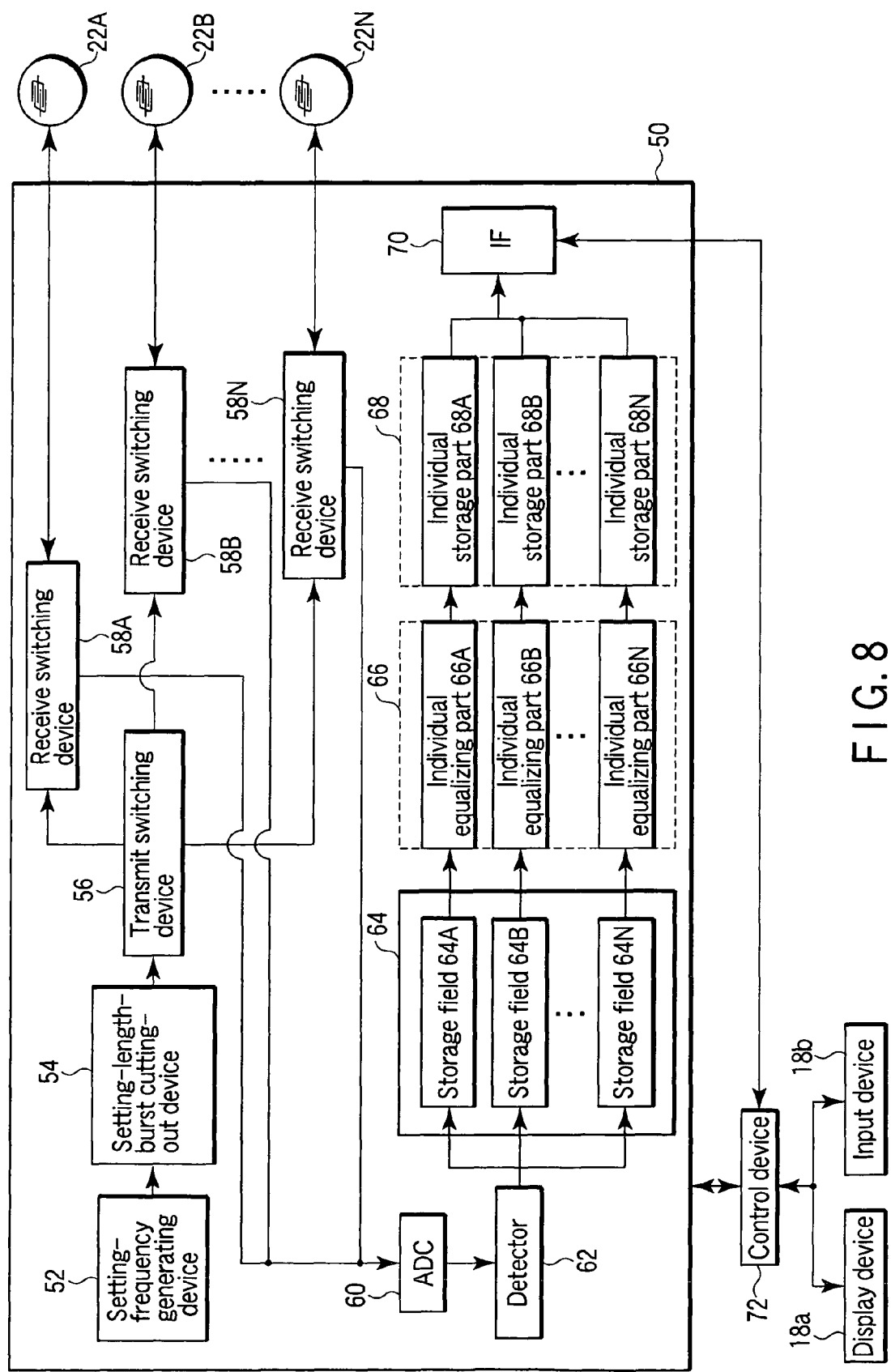
FIG. 8 is a block diagram schematically showing a configuration of a surface acoustic wave element control part for the gas detection part of the gas concentration distribution measuring apparatus in FIG. 1.

As shown in FIG. 8, the above described surface acoustic wave element control part 50 of the gas detection part 14 comprises a setting-frequency generating device (high-frequency signal generating means) 52, a setting-length burst cutting-out device 54, a transmit switching device (switching means) 56, receive switching devices 58A, 58B, . . . 58N, an AD converter (ADC) 60, a detector 62, an adding device 64, an equalizing device 66, a storage device 68, and an interface (IF) 70. The surface acoustic wave element control part 50 is accommodated in the outer housing of the gas concentration distribution display unit 18 and connected to a control device 72 for controlling overall operations of the gas concentration distribution measuring apparatus 10, and the display device 18a and an input device 18b of the gas concentration distribution display unit 18 are also connected to the control device 72.

The setting-frequency generating device 52 excites a target frequency fitted to characteristics of the surface acoustic wave element 22 of the gas detector 12 of the gas detection part 14. Here, the single setting-frequency generating device 52 generates a high-frequency signal.

The setting-length burst cutting-out device 54 is a switching device that cuts out the high-frequency signal excited by the setting-frequency generating device 52 at each freely set time. A high-frequency burst signal is thereby produced. The setting-length burst cutting-out device 54 adjusts the time to cut out the high-frequency signal to a time shorter than that necessary for surface acoustic waves to circulate around the surface acoustic wave circulating path 22a at one time. Therefore, signals repeatedly output each time the surface acoustic waves circulate around the surface acoustic wave circulating path 22*a* from each of surface acoustic wave elements 22A to 22N can be separated based on time.

The transmit switching device 56 switches to each of the surface acoustic wave elements 22A to 22N so as to transmit the high-frequency burst signal cut out by the setting-length burst cutting-out device 54 to each of the plurality of the units of comb-shaped electrodes 22*c*. The transmit switching device 56 sequentially switches the input destination of the high-frequency burst signal by taking time longer than the time necessary for the surface acoustic waves to circulate around the surface acoustic wave circulating path 22*a* of each of surface acoustic wave elements 22A to 22N at one time. To provide a supplemental explanation, the switching timing of the input destination of the high-frequency burst signal is proportional to the diameter of the surface acoustic wave circulating path 22*a* of the base member 22*b* of each of the surface acoustic wave elements 22A to 22N. Thus, when the high-frequency burst signal is at 150 MHz, the transmit switching device 56 switches the input destination by taking 1 μs or more if the base member 22*b* of each of surface acoustic wave elements 22A to 22N is a crystal ball of 1 mm in diameter and by taking 3.3 μs or more if the diameter of the base member 22*b* is 3.3 mm.

If the time at which the input destination of the high-frequency burst signal to the surface acoustic wave elements 22A to 22N is switched and the time at which an output signal from the unit of comb-shaped electrodes 22*c* of one of the surface acoustic wave elements 22A to 22N is detected match, the transmit switching device 56 waits to input the high-frequency burst signal. This prevents the input signal from obstructing detection of the output signal so as to detect the output signal with high precision.

The receive switching devices 58A to 58N are provided to correspond to the surface acoustic wave elements 22A to 22N, and decide the timing to pick up a circulating signal of the surface acoustic waves, the surface acoustic waves being excited and circulated along the surface acoustic wave circulating path 22*a* of each of the surface acoustic wave elements 22A to 22N, from the unit of comb-shaped electrodes 22*c* of each of the surface acoustic wave elements 22A to 22N. Here, each of the receive switching devices 58A to 58N picks up an one-hundred-time output signal as a signal to be analyzed from the surface acoustic wave circulating path 22*a* of each of the surface acoustic wave elements 22A to 22N with the unit of comb-shaped electrodes 22*c*. The output signal picked up from each of the surface acoustic wave elements 22A to 22N is sent to the AD converter 60. The one-hundred-time output signal described above is only one example, and the number of times of circulation at which the output signal to be analyzed is picked up from the surface acoustic wave circulating path 22*a* of each of the surface acoustic wave elements 22A to 22N through the unit of comb-shaped electrodes 22*c* may be freely set depending on characteristics of each of the surface acoustic wave elements 22A to 22N and the contents to be analyzed from the output signal.

The AD converter (ADC) 60 converts the above described output signal of analog into a digital signal. Here, the analog signal to be inputted to the AD converter (ADC) 60 may be an analog signal after the frequency of the high-frequency signal is down-converted by the heterodyne method.

Hi-frequency burst signals are inputted to the units of comb-shaped electrodes 22*c* of the surface acoustic wave elements 22A to 22N by the transmit switching device 56 with a time difference. Thus, the output signal picked up from the unit of comb-shaped electrodes 22*c* of each of the surface acoustic wave elements 22A to 22N come into the AD converter 60 while the transmit switching device 56 stops its switching operation. As a result, the output signals from the surface acoustic wave elements 22A to 22N are separate from each other, and thus, only one AD converter 60 needs to be used.

The detector 62 converts the output signal digitized by the AD converter 60 into data of the phase and that of the strength by operations.

Input of high-frequency burst signals to the first surface acoustic wave element 22A to the last surface acoustic wave element 22N is repeated the "number of equalization" set by the control device 72.

The adding device 64 adds data of the phase and strength of the "number of equalization" converted by the detector 62 from an output signal of the predetermined number of circulation from the unit of comb-shaped electrodes 22*c* of each of the surface acoustic wave elements 22A to 22N through the AD converter 60. The adding device 64 has storage fields 64A to 64N corresponding to the surface acoustic wave elements 22A to 22N, and each of the storage fields 64A to 64N temporarily stores the data added thereto. The adding device 64 also has a function to operate data.

The equalizing device 66 comprises individual equalizing parts 66A to 66N corresponding to the storage fields 64A to 64N. Each of the individual equalizing parts 66A to 66N equalizes the output signals of the "number of equalization" from each of the surface acoustic wave elements 22A to 22N after input of the high-frequency burst signals to the first surface acoustic wave element 22A to the last surface acoustic wave element 22N is repeated the "number of equalization" set by the control device 72. More specifically, each of the individual equalizing parts 66A to 66N equalizes the phase data and strength data after the phase and strength data of the number of equalization corresponding to the output signals of the number of equalization and stored in each of the corresponding storage fields 64A to 64N in the adding device 64 are added.

To provide a supplemental explanation, the above described data obtained by using only one out-put signal from each of the surface acoustic wave elements 22A to 22N may include an influence of noise. Therefore, in order to minimize the influence of noise as much as possible, the phase data and strength data equalized by using the out-put signals of the number of equalization from each of the surface acoustic wave elements 22A to 22N as described above is obtained.

That is, after phase and strength data of digital signals corresponding to an output signal of a predetermined number of circulation from the n-th last surface acoustic wave element 22N is stored, measurement of phase and strength data of digital signals corresponding to output signals of the predetermined number of circulation of each of the first surface acoustic wave element 22A to the last surface acoustic wave element 22N is restarted until the number of the measurement reaches the number of equalization.

In the meantime, measurement of the data of each of the first surface acoustic wave element 12A to the last surface acoustic wave element 12N performed each time after the second time needs to be performed after an influence of surface acoustic waves excited and circulated last time in each of the first surface acoustic wave element 12A to the last surface acoustic wave element 12N has disappeared. More specifically, if the frequency of a high-frequency burst signal inputted to each of the surface acoustic wave elements 12A to 12N each of which uses a crystal ball of 1 mm in diameter as the base member 22*b* is 150 MHz, it is sufficient to set 1 ms or more between the last time at which a high-frequency burst signal is inputted to each of the surface acoustic wave elements 12A to 12N and the next time at which a high-frequency burst signal is inputted to each of the surface acoustic wave elements 12A to 12N.

Instead of obtaining equalized values of the data of each of the plurality of surface acoustic wave elements 22A to 22N by using the plurality of individual equalizing parts 66A to 66N corresponding to the plurality of surface acoustic wave elements 22A to 22N, as described above, the equalized values of the data can be obtained by using an equalizing device which does not comprise the plurality of individual equalizing parts 66A to 66N but comprises one common equalizing part corresponding to the plurality of surface acoustic wave elements 22A to 22N. In this equalizing device, the common equalizing part is corresponded sequentially to each of the plurality of surface acoustic wave elements 22A to 22N, especially to each of the storage fields 64A to 64N corresponding to the plurality of surface acoustic wave elements 22A to 22N, to obtain equalized value of the data added to each of the storage fields 64A to 64N.

The storage device 68 comprises a plurality of individual storage parts 68A to 68N corresponding to the plurality of individual equalizing parts 66A to 66N of the equalizing device 66. The plurality of individual storage parts 68A to 68N store values of the data equalized by the plurality of individual equalizing parts 66A to 66N corresponding thereto.

In addition to values of the data equalized by the plurality of corresponding individual equalizing parts 66A to 66N, each of the plurality of individual storage parts 68A to 68N has a region to store attached data corresponding to each of the plurality of surface acoustic wave elements 22A to 22N.

Here, the plurality of individual storage parts 68A to 68N are provided to correspond to the plurality of individual equalizing parts 66A to 66N of the plurality of surface acoustic wave elements 22A to 22N. However, the storage device 68 may be configured to include only one storage part, in which values of the data equalized by the plurality of individual equalizing parts 66A to 66N or values of the data equalized, as described above, by the equalizing device using only one common equalizing part corresponding to the plurality of surface acoustic wave elements 22A to 22N can be stored separately by assigning mutually different addresses to these values.

The storage device 68 may be configured to transmit data to an external processing device (not shown) such as a personal computer (PC).

The interface (IF) 70 enables relaying of various kinds of data between each of the various devices 52 to 68 described above and the control device 72 that controls overall operations of the gas concentration distribution measuring apparatus 10. More specifically, the interface 70 enables transfer of instructions and data through either wire communication or radio, such as USB, Ethernet (registered trademark), Bluetooth (registered trademark), IEEE-1394, PHS, WCDMA, CDMA2000, and IEEE-802.xx. The interface 70 also enable the gas concentration distribution measuring apparatus 10 to operate with the other gas concentration distribution measuring apparatus 10.

The control device 72 performs to control frequency of the high-frequency signal excited in the setting-frequency generating device 52, to adjustment the time length for the setting-length burst cutting-out device 54 to cut out the high-frequency signal, to control the switching of the transmit switching device 56 to each of the surface acoustic wave elements 22A to 22N, and to control the switching of the receive switching devices 58A to 58N to the surface acoustic wave elements 22A to 22N, and starts measurement of the concentration of the predetermined gas by using the plurality of gas detectors 22A to 22N of the gas detection part 14.

More specifically, after the high-frequency signal in burst form having the predetermined length cut out from the high-frequency signal oscillated by the setting-frequency generating device 52 by the setting-length burst cutting-out device 54 is inputted to the first surface acoustic wave element 22A, the control device 72 controls the transmit switching device 56 in such a way that the input destination of the high-frequency signal in burst form having the predetermined length is switched to the second and subsequent surface acoustic wave elements 22B to 22N in turn before detecting an output signal of the surface acoustic waves of the predetermined number of circulation from the first surface acoustic wave element 22A.

The control device 72 sets the "number of equalization" which is the number of times by which a high-frequency burst signal is inputted to the first surface acoustic wave element 22A to the last surface acoustic wave element 22N, and controls operations of the individual equalizing parts 66A to 66N of the equalizing device 66. The control device 72 further measures characteristics (that is, the concentration of the predetermined gas) of the surface acoustic waves after circulating around the surface acoustic wave circulating path 22a of each of the plurality of surface acoustic wave elements 22A to 22N the predetermined number of times, based on the phase and strength data of the digital signals corresponding to the output signal from each of the plurality of surface acoustic wave elements 22A to 22N after being equalized by the individual equalizing parts 66A to 66N of the equalizing device 66.

The control device 72 makes the display device 18a display the above measurement results, and performs accepting data input and handling errors of input values through the input device 18b.

The control device 72 may have functions to store and manage the above measurement results in an external storage device (not shown) through the interface 70, to automatically form a report based on the above measurement results, or to open publish the above measurement results via the Internet.

The control device 72 may further be configured to control operations of the other gas concentration distribution measuring apparatus 10 connected thereto via the interface 70.

The input device 18b may be a keyboard, a mouse, a dedicated input device, or a touch-sensitive input device provided on the screen of the display device 18a.

Operations of the gas detection part 14 controlled by the surface acoustic wave element control part 50 configured as described above will be described with reference to the flow chart in FIG. 9 and the signal correlation diagram in FIG. 10.

First, a high-frequency signal of the target frequency fitted to characteristics of the plurality of surface acoustic wave elements 22A to 22N is generated by the setting-frequency generating device 52 (step S1). Here, if the high-frequency signal is inputted to the first surface acoustic wave element 22A for the first time, a high-frequency signal in burst form having a desired length is created from the high-frequency signal by the setting-length burst cutting-out device 54 (step S2—YES, step S3). The setting-length burst cutting-out device 54 creates a high-frequency signal in burst form (high-frequency burst signal) whose length is shorter than a circulation time needed for surface acoustic waves excited from the high-frequency signal in burst form and propagated to circulate along the surface acoustic wave circulating path 22a, so that output signals picked up after circulating along the surface acoustic wave circulating paths 22a of the plurality of surface acoustic wave elements 22A to 22N the predetermined number of circulation are separated from each other with a time difference.

Next, the high-frequency burst signal is inputted to the unit of comb-shaped electrodes 22c of the first surface acoustic wave element 22A through the receive switching device 58A selected by the transmit switching device 56.

After the high-frequency burst signal is inputted to the unit of comb-shaped electrodes 22c of the first surface acoustic wave element 22A, the transmit switching device 56 switches the input destination of the high-frequency burst signal to the unit of comb-shaped electrodes 22c of the other surface acoustic wave elements 22B to 22N in turn before the surface acoustic waves excited by the first inputted high-frequency burst signal and propagated along the surface acoustic wave circulating path 22a of the first surface acoustic wave element 22A is picked up from the unit of comb-shaped electrodes 22c after the first excited surface acoustic waves circulate the predetermined number (step S4).

When the high-frequency burst signal is inputted to the units of comb-shaped electrodes 22c of the plurality of surface acoustic wave elements 22A to 22N, surface acoustic waves are excited on the surface acoustic wave circulating paths 22a of the plurality of surface acoustic wave elements 22A to 22N and continue to circulate along the surface acoustic wave circulating paths 22a.

After the surface acoustic waves first excited and circulated around the surface acoustic wave circulating path 22a of the first surface acoustic wave element 22A is picked up through the unit of comb-shaped electrodes 22c and the receive switching device 58A after the first excited surface acoustic waves circulate the predetermined number, the surface acoustic waves excited and circulated along the surface acoustic wave circulating paths 22a of the second surface acoustic wave element 22B to the last surface acoustic wave element 22N are detected and picked up in turn through the units of comb-shaped electrodes 22c and the corresponding receive switching devices 58B to 58N after each of the second excited and last excited surface acoustic waves circulates the predetermined number (step S5—Yes).

Here, the output signal received by the unit of comb-shaped electrodes 22c when the surface acoustic waves circulate along the surface acoustic wave circulating path 22a one hundred times is to be measured, and thus, the output signals will be detected and picked up in turn from the unit of comb-shaped electrodes 22c of the first surface acoustic wave element 22A to the unit of comb-shaped electrodes 22c of the last surface acoustic wave element 22N when 100 μs or more elapse after the first high-frequency burst signal is inputted to the unit of comb-shaped electrodes 22c of the first surface acoustic wave element 22A.

After the number of times of receiving the output signal is counted (step S6), the output signal is digitized by the AD converter 60 and phase data and strength data are obtained from the digitized output signal by the detector 62 (step S7). Then, as described above, the data is distributed to one of the plurality of storage fields 64A to 64N of the adding device 64 depending on the number of counting (step S8).

When the number of counting becomes equal to the number of the plurality of surface acoustic wave elements 22A to 22N, as described above, the number of counting is reset (step S9—YES, S10). As a result, as described above, the number of counting and the output signals from the units of comb-shaped electrodes 22c of the plurality of surface acoustic wave elements 22A to 22N can be associated.

Subsequently, the predetermined high-frequency burst signals for the number of equalization preset are inputted to each of the plurality of surface acoustic wave elements 22A to 22N in turn (step S11—NO).

About 1 ms is needed until the output signal generated by the surface acoustic waves circulating along the surface acoustic wave circulating path 22a of each of the plurality of surface acoustic wave elements 22A to 22N substantially disappears after the high-frequency burst signal is inputted. Therefore, each of the second and subsequent inputs of the high-frequency burst signal to the surface acoustic wave circulating path 22a of each of the plurality of surface acoustic wave elements 22A to 22N is performed when 1 ms or more elapses after the last input (step S12). That is, when the high-frequency burst signal is inputted to the first surface acoustic wave element 22A next time after the high-frequency burst signal is inputted to the first surface acoustic wave element 22A last time, the control device 72 determines whether 1 ms or more has passed since the high-frequency burst signal was inputted to the first surface acoustic wave element 22A last time, and, if 1 ms or more has not passed (step S12—NO), the control device 72 waits until 1 ms passes. The control device 72 also determines whether the timing to input the high-frequency burst signal to the surface acoustic wave circulating path 22a of each of the plurality of surface acoustic wave elements 22A to 22N overlaps with the detection timing at step S5 and, if both timings overlap, shifts the timing to input the high-frequency burst signal to avoid overlapping (step S13). Then, the control device 72 proceeds to step S3.

When the above described steps S3 to S13 are performed for the number of equalization (step S11—YES), the data obtained by adding the above data from each of the plurality of surface acoustic wave elements 22A to 22N to the corresponding storage fields 64A to 64N of the adding device 64 the number of equalization is calculated by the corresponding individual equalizing parts 66A to 66N of the equalizing device 66 based on the number of equalization to obtain average values (step S14). The average values of the data calculated in this manner are stored in the individual storage parts 68A to 68N corresponding to the surface acoustic wave elements 22A to 22N it the storage device 68.

Subsequently, the above described steps S3 to S14 are performed until the gas concentration distribution measuring apparatus 10 finishes measurement of the concentration of the predetermined gas in the desired space region (step S5).

[Operation of the Gas Concentration Distribution Measuring Apparatus and Technical Advantage Thereof]

As described above, in the gas concentration distribution measuring apparatus 10 according to the embodiment, when the high-frequency burst signal is inputted to the first surface acoustic wave element 22A, the input destination of the high-frequency burst signal is switched to the other surface acoustic wave elements 22B to 22N in turn before an output signal from the surface acoustic waves that has circulated in the first surface acoustic wave element 22A the predetermined number of circulation is detected for the first time. Then, after the output signal from the surface acoustic waves that has circulated in the first surface acoustic wave element 22A the predetermined number is detected for the first time, the output signal from the surface acoustic waves that has circulated in each of the surface acoustic wave elements 22B to 22N the predetermined number is detected in turn.

As a result, if, in the gas concentration distribution measuring apparatus 10 according to the present embodiment, the output signals of the surface acoustic waves each of which have circulated the predetermined number, from all of the plurality of surface acoustic wave elements 22A to 22N to each of which the predetermined high-frequency burst signal is inputted from the single setting-frequency generating device 52 through the setting-length burst cutting-out device 54 are detected, the time needed until the output signals of the surface acoustic waves each of which has circulated the predetermined number, from all of the plurality of surface acoustic wave elements 22A to 22N are detected can be reduced in comparison with a case in which inputting a predetermined high-frequency burst signal to one surface acoustic wave element and detecting an output signal of a surface acoustic wave that has circulated the predetermined number from the one surface acoustic wave element, then inputting the predetermined high-frequency burst signal to the next one surface acoustic wave element and detecting an output signal of a surface acoustic wave that has circulated the predetermined number from the next one surface acoustic wave element, are repeated as many times as the number of surface acoustic wave elements.

An example will be explained below.

In this example, the diameter of the spherical base member of each of the plurality of surface acoustic wave elements 22A to 22N to be used is 1 mm, and the switching timing of the transmit switching device 56 for the plurality of the receive switching devices 58A to 58N corresponding to the plurality of surface acoustic wave elements 22A to 22N is 1 µs. Then, the output signal of the surface acoustic waves circulated the predetermined number is detected 256 times from each of the plurality of surface acoustic wave elements 22A to 22N, 256 pieces of the phase data and 256 pieces of the strength data in 256 pieces of the digitized output signals obtained from each output signal through the AD converter 60 and the detector 62 are added to a corresponding one of the plurality of the storage fields 64A to 64N in the adding device 64, and further, the added phase data and strength data are equalized in a corresponding one of the plurality of individual equalizing parts 66A to 66N in the equalizing device 66. When an output signal of surface acoustic waves that has circulated the predetermined number is detected from one surface acoustic wave element next time, in order to prevent an output signal of surface acoustic waves that has circulated the predetermined number, detected from the one surface acoustic wave element last time, from influencing the output signal detected from the one surface acoustic wave element the next time, a predetermined high-frequency burst signal is inputted to the one surface acoustic wave element next time after 1 ms elapsing from the last input of the predetermined high-frequency burst signal to the one surface acoustic wave element.

Then, the predetermined number of circulation of surface acoustic waves when an output signal of the surface acoustic waves is obtained to obtain the aforementioned data from one surface acoustic wave element is set to 100.

The time needed for surface acoustic waves to circulate along the surface acoustic wave circulating path 22a of the spherical base member 22b of 1 mm in diameter of a surface acoustic wave element is 1 µs. And, as described above, the time during which an influence of a surface acoustic wave excited and propagated last time in one surface acoustic wave element disappears is 1 ms. Then, if the transmit switching device 56 switches the surface acoustic wave element to which a high-frequency burst signal of a predetermined length is inputted every 1 µs, a high-frequency burst signal of the predetermined length can be inputted to 1000 surface acoustic wave elements during 1 ms elapses.

Therefore, when detection of an output signal of surface acoustic waves that has circulated the predetermined number from one surface acoustic wave element is repeated 256 times and, as described above, average values of the phase data and strength data are determined from each of the 256 output signals, the time of 256 (times)×1 ms=256 ms is needed because the high-frequency burst signal of the predetermined length needs to be inputted to the one surface acoustic wave element repeatedly at least, as described above, every 1 ms.

However, as described above, if the high-frequency burst signal of the predetermined length to one surface acoustic wave element every 1 µs, the high-frequency burst signal of the predetermined length can be inputted to 1000 surface acoustic wave elements in 1 ms.

In contrast, as described above, when detection of an output signal of surface acoustic waves that has circulated the predetermined number from one surface acoustic wave element is repeated 256 times and average values of data of the phase and strength are determined, as described above, from the 256 output signals and then, a predetermined high-frequency burst signal is inputted to the next surface acoustic wave element, the high-frequency burst signal of the predetermined length can be inputted to one surface acoustic wave element only every 256 ms.

That is, when the former case and the latter case are compared with each other, it is obvious that the former case needs a far shorter time to determine average values from all surface acoustic wave elements by using the same number of surface acoustic wave elements than the latter case.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gas concentration distribution measuring apparatus, comprising:

a gas detection part which includes a plurality of gas detectors provided at a plurality of mutually different positions to measure a concentration of a predetermined gas, and which moves while maintaining relative positions of the plurality of gas detectors;

a gas detector position information measuring part which measures position information of the plurality of gas detectors of the gas detection part; and a gas concentration distribution display unit to which measured values of gas concentrations measured by the plurality of gas detectors of the gas detection part and position information of the plurality of gas detectors measured by the gas detector position information measuring part when the plurality of gas detectors finish measurement of gas concentrations are inputted, and which displays a distribution of concentrations of the predetermined gas in a space, in which the gas detection part moves, based on the measured values of the gas concentrations and the position information of the gas detectors, wherein each gas detector includes a surface acoustic wave element including at least one surface acoustic wave circulating path which is circularly continuous with a portion of a spherical shape and along which a surface acoustic wave is capable to circulate, and each gas detector includes a filter which covers the surface acoustic wave element and which prevents foreign matter excluding gases from coming into contact with the surface acoustic wave circulating path of the surface acoustic wave element, and a gas exchange element which exchanges a gas contained in a space enclosed by the filter for a gas in an outer space surrounding the filter.

2. The gas concentration distribution measuring apparatus according to claim 1, wherein the gas detector position information measuring part includes at least one of an acceleration sensor and an angular velocity sensor.

3. The gas concentration distribution measuring apparatus according to claim 1, wherein
each gas detector includes at least two surface acoustic wave elements, and
at least a portion of the surface acoustic wave circulating path of one surface acoustic wave element is covered with a gas sensitive layer sensitive to the gas and the whole surface acoustic wave circulating path of the other surface acoustic wave element is exposed to the gas.

4. The gas concentration distribution measuring apparatus according to claim 1, wherein
each gas detector includes a plurality of the surface acoustic wave elements, and
at least a portion of the surface acoustic wave circulating path of each of the plurality of surface acoustic wave elements is covered with a gas sensitive layer sensitive to only a mutually different specific gas.

5. The gas concentration distribution measuring apparatus according to claim 4, wherein each gas detector includes one surface acoustic wave element having the surface acoustic wave circulating path which is wholly exposed to the gas.

6. The gas concentration distribution measuring apparatus according to claim 1, wherein
the plurality of gas detectors are two-dimensionally arranged in the gas detection part, and
the gas concentration distribution display unit displays the distribution of concentrations of the predetermined gas in a three-dimensional space through which the gas detection part has moved.

7. The gas concentration distribution measuring apparatus according to claim 6, wherein each gas detector includes a surface acoustic wave element including at least one surface acoustic wave circulating path which is circularly continuous with a portion of a spherical shape and along which a surface acoustic wave is capable to circulate.

8. The gas concentration distribution measuring apparatus according to claim 7, wherein each gas detector includes a filter which covers the surface acoustic wave element and which prevents foreign matter excluding gases from coming into contact with the surface acoustic wave circulating path of the surface acoustic wave element, and a gas exchange element which exchanges a gas contained in a space enclosed by the filter for a gas in an outer space surrounding the filter.

9. The gas concentration distribution measuring apparatus according to claim 7, wherein
each gas detector includes at least two surface acoustic wave elements, and
at least a portion of the surface acoustic wave circulating path of one surface acoustic wave element is covered with a gas sensitive layer sensitive to the gas, and the whole surface acoustic wave circulating path of the other surface acoustic wave element is exposed to the gas.

10. The gas concentration distribution measuring apparatus according to claim 7, wherein
each gas detector includes a plurality of the surface acoustic wave elements, and
at least a portion of the surface acoustic wave circulating path of each of the plurality of surface acoustic wave elements is covered with a gas sensitive layer sensitive to only a mutually different specific gas.

11. The gas concentration distribution measuring apparatus according to claim 10, wherein each gas detector includes one surface acoustic wave element having the surface acoustic wave circulating path which is wholly exposed to the gas.

12. A gas concentration distribution measuring apparatus, comprising:
a gas detection part which includes a plurality of gas detectors provided at a plurality of mutually different positions to measure a concentration of a predetermined gas, and which moves while maintaining relative positions of the plurality of gas detectors;
a gas detector position information measuring part which measures position information of the plurality of gas detectors of the gas detection part; and
a gas concentration distribution display unit to which measured values of gas concentrations measured by the plurality of gas detectors of the gas detection part and position information of the plurality of gas detectors measured by the gas detector position information measuring part when the plurality of gas detectors finish measurement of gas concentrations are inputted, and which displays a distribution of concentrations of the predetermined gas in a space, in which the gas detection part moves, based on the measured values of the gas concentrations and the position information of the gas detectors, wherein
the plurality of gas detectors are linearly arranged in the gas detection part, and
the gas concentration distribution display unit displays the distribution of concentrations of the predetermined gas in a two-dimensional space through which the gas detection part has moved.

13. The gas concentration distribution measuring apparatus according to claim 12, wherein each gas detector includes a surface acoustic wave element including at least one surface acoustic wave circulating path which is circularly continuous with a portion of a spherical shape and along which a surface acoustic wave is capable to circulate.

14. The gas concentration distribution measuring apparatus according to claim 13, wherein each gas detector includes a filter which covers the surface acoustic wave element and which prevents foreign matter excluding gases from coming into contact with the surface acoustic wave circulating path of the surface acoustic wave element, and a gas exchange element which exchanges a gas contained in a space enclosed by the filter for a gas in an outer space surrounding the filter.

15. The gas concentration distribution measuring apparatus according to claim 13, wherein
each gas detector includes at least two surface acoustic wave elements, and
at least a portion of the surface acoustic wave circulating path of one surface acoustic wave element is covered with a gas sensitive layer sensitive to the gas and the whole surface acoustic wave circulating path of the other surface acoustic wave element is exposed to the gas.

16. The gas concentration distribution measuring apparatus according to claim 13, wherein
each gas detector includes a plurality of the surface acoustic wave elements, and
at least a portion of the surface acoustic wave circulating path of each of the plurality of surface acoustic wave elements is covered with a gas sensitive layer sensitive to only a mutually different specific gas.

17. The gas concentration distribution measuring apparatus according to claim 16, wherein each gas detector includes one surface acoustic wave element having the surface acoustic wave circulating path which is wholly exposed to the gas.

* * * * *